(12) United States Patent
Smart et al.

(10) Patent No.: US 9,701,987 B2
(45) Date of Patent: Jul. 11, 2017

(54) FERMENTATION PROCESS FOR THE PRODUCTION AND CONTROL OF PYRUVATE-DERIVED PRODUCTS

(71) Applicant: LanzaTech New Zealand Limited, Skokie, IL (US)

(72) Inventors: Kathleen Frances Smart, Skokie, IL (US); Boi San Ly, Skokie, IL (US)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 14/283,287

(22) Filed: May 21, 2014

(65) Prior Publication Data

US 2015/0337341 A1    Nov. 26, 2015

(51) Int. Cl.

| C12P 7/18 | (2006.01) |
|---|---|
| C12P 7/06 | (2006.01) |
| C12P 7/16 | (2006.01) |
| C12P 7/44 | (2006.01) |
| C12P 7/56 | (2006.01) |
| C12P 7/26 | (2006.01) |
| C12P 7/46 | (2006.01) |

(52) U.S. Cl.
CPC ............... *C12P 7/18* (2013.01); *C12P 7/065* (2013.01); *C12P 7/16* (2013.01); *C12P 7/26* (2013.01); *C12P 7/46* (2013.01); *C12P 7/56* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| 5,173,429 A | 12/1992 | Gaddy et al. |
|---|---|---|
| 5,593,886 A | 1/1997 | Gaddy |
| 5,807,722 A | 9/1998 | Gaddy |

(Continued)

FOREIGN PATENT DOCUMENTS

NZ    WO 2012131627 A1 * 10/2012 ............. C12P 7/18

OTHER PUBLICATIONS

PATRIC Pathosystems Resource Integration Center: Comparative Pathway Map for Clostridium autoethanogenum DSM 10061, accessed on Nov. 2, 2015, available at www.patricbrc.org/portal/portal/patric/CompPathwayMap?cType=genome&cId=1341692.3&dm=feature&feature_id=PATRIC.1341692.3.ASZX01000049.CDS.8102.8881.rev&map=00770&algorithm=PATRIC&ec_number=.*
DSMZ 640, DSMZ GmbH, Germany, 640. Caldicellulosiruptor Medium, Copyright 2015, available at www.dsmz.de/microorganisms/medium/pdf/DSMZ_Medium640.pdf.*
DSMZ 320, DSMZ GmbH, Germany, 320. Clostrdium Celluovorans Medium, Copyright 2012, available at www.dsmz.de/microorganisms/medium/pdf/DSMZ_Medium320.pdf.*

(Continued)

*Primary Examiner* — Robert Yamasaki
*Assistant Examiner* — Charles Zoltan Constantine
(74) *Attorney, Agent, or Firm* — Frank S Molinaro

(57) ABSTRACT

A process for producing and controlling pyruvate derived products during the fermentation of a CO containing substrate by an acetogenic carboxydotrophic microorganism has been developed. The process involves increasing the concentration of at least one nutrient selected from the group consisting of vitamin B1, vitamin B5, vitamin B7 and mixtures thereof above the cellular requirement of the microorganism. When the concentration is increased, the production of 2,3-butanediol (2,3-BDO) increases whereas the production of the other metabolites is virtually unchanged. The effect is reversible so that when the concentration is decreased, the production of 2,3-BDO is also decreased. This allows one to control the ratio of ethanol:2,3-BDO to a desired value which can vary from about 4:1 to about 1:2.

14 Claims, 4 Drawing Sheets

(56) References Cited

U.S. PATENT DOCUMENTS

| | | |
|---|---|---|
| 5,821,111 A | 10/1998 | Grady et al. |
| 6,136,577 A | 10/2000 | Gaddy |
| 6,340,581 B1 | 1/2002 | Gaddy |
| 6,368,819 B1 | 4/2002 | Gaddy et al. |
| 6,753,170 B2 | 6/2004 | Gaddy et al. |
| 8,143,037 B2 | 3/2012 | Zahn et al. |
| 8,376,736 B2 | 2/2013 | Simpson et al. |
| 9,012,190 B2 | 4/2015 | Dauner et al. |
| 2013/0045517 A1 | 2/2013 | Coombes |
| 2013/0203143 A1 | 8/2013 | Schultz et al. |
| 2013/0210096 A1 | 8/2013 | Schultz et al. |

OTHER PUBLICATIONS

Khamaiseh, Emran I. et al., Enhanced butanol production by Clostridium ecetobutylicum NCIMB 13357 grown on date fruit as carbon source in P2 medium, The Scientific World Journal, Jan. 6, 2014, vol. 2014, Article ID. 395754, (internal pp. 1-7).

Survase, Shrikant A. et al., Market refused vegetables as a supplement for improved acetone-butanol-ethanol production by Clostridium acetobutylicum DSM 792, Industrial Crops and Products, 2013, vol. 45, pp. 349-354.

International Search Report for International Patent Application PCT/US2015/031857, Korean Intellectual Property Office, Jul. 29, 2015.

\* cited by examiner

FERMENTATION PROCESS FOR THE PRODUCTION AND CONTROL OF PYRUVATE-DERIVED PRODUCTS

FIELD

The present invention relates to methods for altering the metabolite profile of a fermentation system through adjusting the concentration of key nutrients in a liquid nutrient medium. In particular, the invention relates to methods for increasing the production of 2,3-butanediol in a fermentation process.

BACKGROUND OF THE INVENTION

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Alcohols suitable for use as biofuels include ethanol, butanol and 2,3-butanediol.

Ethanol is rapidly becoming a major hydrogen-rich liquid transport fuel around the world. Worldwide consumption of ethanol in 2002 was an estimated 10.8 billion gallons. The global market for the fuel ethanol industry is also predicted to grow sharply in future, due to an increased interest in ethanol in Europe, Japan, the USA and several developing nations.

Butanediols including 1,2-butanediol, 1,3-butanediol, 1,4-butanediol and 2,3-butanediol may be considered to have a variety of advantages over ethanol. Like ethanol, butanediols may be used directly as an automotive fuel additive. They may also be relatively easily transformed into a number of other potentially higher value and/or higher energy products. For example, 2,3-butanediol may be readily converted in a two step process into an eight-carbon dimer which can be used as aviation fuel.

2,3-butanediol derives its versatility from its di-functional backbone, i.e., 2 hydroxyl groups are located at vicinal C-atoms allowing the molecule to be transformed quite easily into substances such as butadiene, butadione, acetoin, methylethyl ketone etc. These chemical compounds are used as base molecules to manufacture a vast range of industrially produced chemicals.

In addition, 2,3-butanediol may be used as a fuel in an internal combustion engine. It is in several ways more similar to gasoline than it is to ethanol. As the interest in the production and application of environmentally sustainable fuels has strengthened, interest in biological processes to produce 2,3-butanediol (often referred to as bio-butanol) has increased.

Carbon Monoxide (CO) is a major by-product of the incomplete combustion of organic materials such as coal or oil and oil derived products. Although the complete combustion of carbon containing precursors yields CO2 and water as the only end products, some industrial processes need elevated temperatures favouring the build up of carbon monoxide over CO2. One example is the steel industry, where high temperatures are needed to generate desired steel qualities. For example, the steel industry in Australia is reported to produce and release into the atmosphere over 500,000 tonnes of CO annually.

Furthermore, CO is also a major component of syngas, where varying amounts of CO and H2 are generated by gasification of a carbon-containing fuel. For example, syngas may be produced by cracking the organic biomass of waste woods and timber to generate precursors for the production of fuels and more complex chemicals.

The release of CO into the atmosphere may have significant environmental impact. In addition, emissions taxes may be required to be paid, increasing costs to industrial plants. Since CO is a reactive energy rich molecule, it can be used as a precursor compound for the production of a variety of chemicals. However, this valuable feedstock has not been utilised to produce 2,3-butanediol.

It has been demonstrated that 2,3-butanediol can be produced by microbial fermentation of carbohydrate containing feedstock (Syu M J, *Appl Microbiol Biotechnol* 55:10-18 (2001), Qin et al., *Chinese J Chem Eng* 14(1):132-136 (2006)). 2,3-butanediol may also be produced by microbial fermentation of biomass from crops such as sugar beet, corn, wheat and sugarcane. However, the cost of these carbohydrate feed stocks is influenced by their value as human food or animal feed and the cultivation of starch or sucrose-producing crops for 2,3-butanediol production is not economically sustainable in all geographies. Therefore, it is of interest to develop technologies to convert lower cost and/or more abundant carbon resources into 2,3-butanediol.

Production of 2,3-butanediol by microbial fermentation of gaseous substrates comprising CO has been demonstrated. However, the production of 2,3-butanediol by these processes has been a secondary product. Production of other products including ethanol is favoured in fermentation. Butanediol has greater value than the other products produced in such fermentations. It is desirable to be able to affect the fermentation in such a way that the production of 2,3-butanediol is increased. It has previously been shown that increased 2,3-butandiol productivity was influenced by a rate of hydrogen consumption by a microbial culture (WO2012131627).

There remains a need on the art to increase the ability to produce valuable products from industrial gaseous substrates in economically beneficial ways. There is a need to enhance the production of 2,3-butanediol relative to the production of other products that are routinely produced in the fermentation of gaseous substrates by carboxydotrophic bacteria.

SUMMARY OF THE INVENTION

The present invention provides a response to the need in the art. The present invention provides methods for controlling the production of pyruvate-derived products by microbial fermentation of gaseous substrates. The present invention further provides methods for increasing the production of pyruvate-derived products relative to acetyl-coA-derived products. In particular embodiments there is provided a method for increasing the production of 2,3-butandiol relative to other fermentation products such as ethanol and acetic acid.

In a first aspect of the invention, there is provided a method of increasing the flux of carbon to pyruvate during microbial fermentation, the method comprising:
  a) Providing a gaseous substrate comprising CO to a bioreactor comprising a culture of at least one acetogenic carboxydotrophic microorganism in a liquid nutrient medium to produce at least one pyruvate derived product and at least acetyl-CoA derived product; and b) Increasing the concentration of at least one nutrient in the liquid nutrient medium to a concentration above the cellular requirements of the at least one acetogenic microorganism such that the flux of carbon to pyruvate is increased, said nutrient selected from the group consisting of:
  1) Vitamin B1;
  2) Vitamin B5; and
  3) Vitamin B7.

In particular embodiments the concentration of at least one nutrient in the liquid nutrient medium is increased in order to increase the production of at least one pyruvate-derived product. In a particular embodiment, increasing the concentration of at least one nutrient in the liquid nutrient medium further increases biomass density in the bioreactor.

In particular embodiments, the concentration of vitamin B1, B5 or B7, or a mixture thereof, is increased in the liquid nutrient medium. In particular embodiments, the concentration of vitamin B1, B5 or B7, or a mixture thereof, is increased beyond the cellular requirements of the at least one microorganism in the liquid nutrient medium. In particular embodiments, the concentration of vitamin B1, B5, or B7, or mixtures thereof, is increased at least two times above the cellular requirements of at least one microorganism in the liquid nutrient medium. In particular embodiments, the concentration of vitamin B1, B5 or B7, or a mixture thereof, is increased at least ten times above the cellular requirements of at least one microorganism in the liquid nutrient medium. In particular embodiments, increasing the concentration of vitamin B1, B5 or B7, or a mixture thereof, in the liquid nutrient medium does not increase biomass density in the bioreactor.

In one embodiment, the at least one pyruvate-derived product is 2,3-butanediol (2,3-BDO). Alternatively, the at least one pyruvate-derived product is selected from the group consisting of lactate, succinate, methyl ethyl ketone (MEK), 2-butanol, propanediol, 2-propanol, isopropanol, acetoin, isobutanol, citramalate, butadiene and poly lactic acid (PLA). In one embodiment, the at least one acetyl-CoA derived product is selected from the group consisting of ethanol, acetic acid, acetone, butanol, isobutylene, 3-hydroxy propionate (3HP) and fatty acids. In further embodiments, the at least one acetyl-CoA derived product is ethanol.

In a second aspect, the invention provides a method of increasing the ratio of 2,3-butanediol to ethanol produced by a microbial fermentation, the method comprising:
  a) Providing a gaseous substrate comprising CO to a bioreactor comprising a culture of at least one acetogenic carboxydotrophic microorganism in a liquid nutrient medium to produce at least 2,3-butanediol and ethanol; and
  b) Increasing the concentration of at least one nutrient in the liquid nutrient medium to a concentration above the cellular requirements of the at least one acetogenic carboxydotrophic microorganism such that the ratio of 2,3-butanediol to ethanol is increased, said nutrient selected from the group consisting of:
    1) Vitamin B1;
    2) Vitamin B5;
    3) Vitamin B7 and mixtures thereof.

In particular embodiments, increasing at least one nutrient in the liquid nutrient medium decreases the ratio of ethanol:2,3-butanediol by increasing the production of 2,3-BDO. In particular embodiments, the ratio of ethanol to 2,3-BDO varies from about 4:1 to about 1:2.

In particular embodiments, the concentration of at least one nutrient in the liquid nutrient medium is increased such that the microorganism produces 2,3-butanediol at a production rate of at least 5 g/L per day or at least 10 g/L per day or at least 20 g/L per day or at least 30 g/L per day.

In particular embodiments, the acetogenic carboxydotrophic microorganism is selected from the group consisting of *Clostridium*, *Moorella*, *Oxobacter*, *Peptostreptococcus*, *Acetobacterium*, *Eubacterium*, or *Butyribacterium*. In various embodiments, the microorganism is selected from the group comprising *Clostridium autoethanogenum*, *Clostridium ljungdahli*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrphoicum*, *Acetobacterium woodii*, *Alkalibaculum bacchi*, *Blautia producta*, *Eubacterium limosum*, *Moorella thermoacetica*, *Sporomusa ovata*, *Sporomusa silvacetica*, *Sporomusa sphaeroides*, *Oxobacter pfennigii* and *Thermoanaerobacter kiuvi*.

In particular embodiments, the acetogenic carboxydotrophic microorganism is *Clostridium autoethanogenum* or *Clostridium ljungdahlii*. In one particular embodiment, the microorganism is *Clostridium autoethanogenum*. In a particular embodiments, the bacterium has the identifying characteristics of accession number DSM10061, DSM19630 or DSM23693. These bacteria have been deposited at the German Resource Centre for Biological Material (DSMZ) whose address is DSMZ GmbH InhoffenstraBe, 7 B, D-38124 Braunschweig, Germany.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

These and other aspects of the present invention, which should be considered in all its novel aspects, will become apparent from the following description, which is given by way of example only, with reference to the accompanying figures, in which.

DETAILED DESCRIPTION OF THE INVENTION

Figure 1:
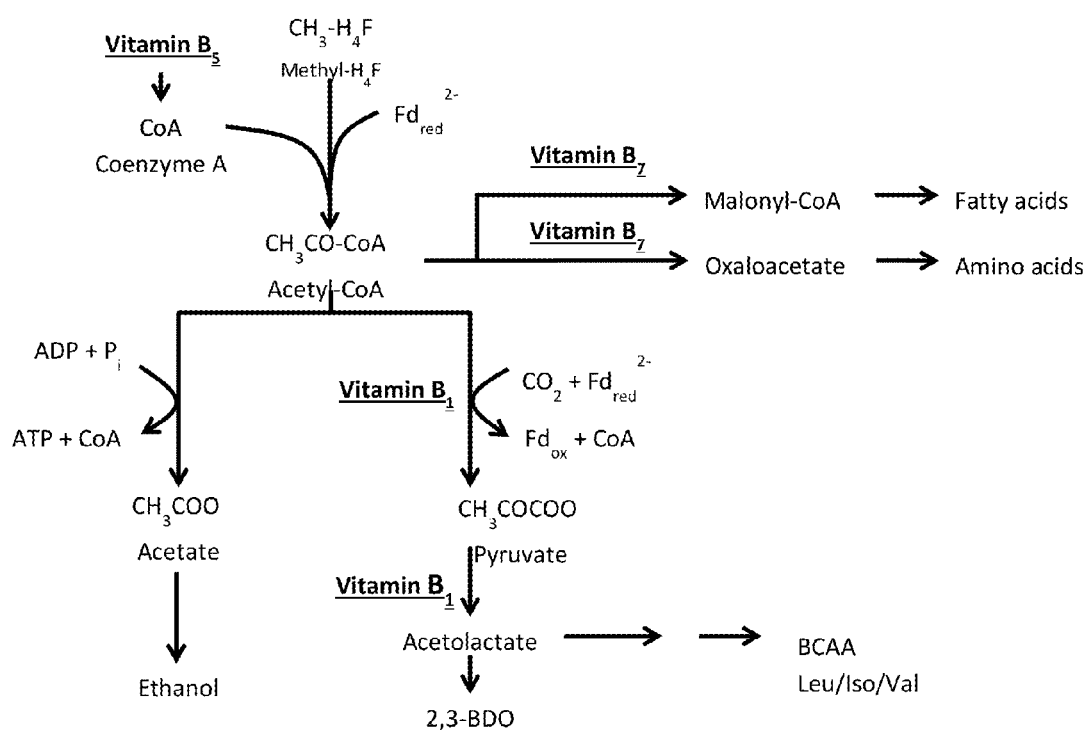
FIG. 1 provides a schematic representation of the ethanol and 2,3-butanediol production pathway in *Clostridium autoethanogenum* and illustrates where vitamins B1, B5 and B7 are utilised as co-factors.

The inventors have devised methods for controlling the metabolic products produced by a culture of at least one acetogenic carboxydotrophic microorganism. In particular, the present invention provides methods for increasing the production of at least one pyruvate-derived product by the microbial fermentation of a gaseous CO substrate by at least one carboxydotrophic acetogenic microorganism.

Definitions

The term "2,3-butanediol" or 2,3-BDO should be interpreted to include all enantiomeric and diastereomeric forms of the compound, including (R,R), (S,S) and meso forms, in racemic, partially stereoisomerically pure and/or substantially stereoisomerically pure forms.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. As is described herein after, in some embodiments the bioreactor may comprise a first growth reactor and a second fermentation reactor. As such, when referring to the addition of a substrate, for example a substrate comprising carbon monoxide, to the bioreactor or fermentation reaction it should be understood to include addition to either or both of these reactors where appropriate.

The term "nutrient" includes any substance that may be utilised in a metabolic pathway of a microorganism. Exemplary nutrients include potassium, B vitamins, trace metals and amino acids.

The term "gaseous substrate" and/or "substrate" include any gas which contains a compound or element used by a microorganism as a carbon source and optionally energy source in fermentation. The gaseous substrate will typically contain a significant proportion of any of CO, $CO_2$, $H_2$ or mixtures thereof.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains a level of carbon monoxide. The gaseous substrate will typically contain a major proportion of CO, preferably at least about 15% to about 95% CO by volume.

"Substrate comprising $CO_2$" includes any substrate stream which contains a level of carbon dioxide. However, it should be appreciated that the gaseous substrate may be provided in alternative forms. For example, the gaseous substrate containing $CO_2$ may be provided dissolved in a liquid. Essentially, a liquid is saturated with a carbon dioxide containing gas and then that liquid is added to the bioreactor. This may be achieved using standard methodology. By way of example, a microbubble dispersion generator (Hensirisak et. al. Scale-up of microbubble dispersion generator for aerobic fermentation; *Applied Biochemistry and Biotechnology* Volume 101, Number 31 October, 2002) could be used. By way of further example, the gaseous substrate containing $CO_2$ and $H_2$ may be adsorbed onto a solid support.

The term "product" as used herein is intended to encompass substances produced by the microbial fermentation. Product can include alcohols, acids or other chemicals. Products can also include gases produced by the microbial fermentation process.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated butanediol concentrations, the volume of desired product produced per volume of substrate consumed, the rate of production or level of production of the desired product, and the relative proportion of the desired product produced compared with other by-products of the fermentation.

The terms "productivity" or "rate of production" is the volumetric productivity of a product. In continuous systems the volumetric productivity is calculated as the ratio of the steady state concentration of the product and the liquid retention time. In batch systems the volumetric productivity is calculated as the concentration and the time required to produce said concentration in a batch system. The volumetric productivity is reported as g/L/day.

Unless the context requires otherwise, the phrases "fermenting", "fermentation process" or "fermentation reaction" and the like, as used herein, are intended to encompass both the growth phase and product biosynthesis phase of the process.

The term "pyruvate derived products" or "products derived from pyruvate" or similar terms as used herein are intended to encompass fermentation products having a pyruvate precursor. These products include, but are not limited to, 2,3-butanediol, lactate, succinate, methyl ethyl ketone (MEK), 2-butanol, propanediol, 2-propanol, isopropanol, acetoin, isobutanol, citramalate, butadiene, and poly lactic acid (PLA).

The term "Acetyl coA derived products" or "products derived from Acetyl coA" or similar terms as used herein are intended to encompass fermentation products having an Acetyl coA precursor. These products include but are not limited to ethanol, acetic acid, acetone, butanol, isobutylene, 3-hydroxy propionate (3HP) and fatty acids.

In the description which follows, 2,3-BDO is used as an example of a pyruvate derived product while ethanol is used as an example of an Acetyl coA derived product. It is to be understood that the invention is not limited to these two specific products but encompasses all the pyruvate and Acetyl coA derived products enumerated above.

Processes for microbial fermentation of gaseous substrates comprising carbon monoxide to produce products such as ethanol and acetate are widely known in the art. Such processes provide a means to produce commercially useful fuels from industrial waste gases comprising CO. These processes generally involve feeding a gaseous substrate comprising CO to a bioreactor comprising a culture of at least one acetogenic carboxydotrophic microorganism in a liquid nutrient medium. The gaseous substrate is anaerobically fermented to produce alcohols, acids and mixtures thereof. The liquid nutrient medium used in the bioreactor typically contains various nutrients that support growth of the at least one acetogenic carboxydotrophic microorganism and are utilised in metabolic pathways of the one or more microorganisms in order to produce alcohols. Examples of such nutrients include MgCl, CaCl, KCl, $H_3PO_4$, Fe, Ni, Zn, Mn, B, W, Se, etc.

It is also known that 2,3-BDO can be produced at various concentrations (usually at a much lower concentration than ethanol) along with ethanol. In certain cases it may be desirable to produce as much 2,3-BDO as possible while in other cases it may be desirable to produce as much ethanol as possible. Surprisingly, the inventors have found that increasing the concentrations of specific nutrients in the liquid nutrient medium, either at start-up of fermentation or at a later point during fermentation, alters the metabolite profile of the fermentation such that production of pyruvate-derived products, e.g. 2,3-BDO is increased while virtually not affecting the production of Acetyl coA derived products, e.g. ethanol. Although the effect has been observed primarily with 2,3-BDO and ethanol, there is no reason to doubt that other pyruvate derived products and Acetyl coA derived products would not be similarly affected. Specific nutrients found to increase pyruvate-derived products when supplied in excess of the cellular requirement necessary for growth and product production are selected from the group consisting of:

1) vitamin B1;
2) vitamin B5;
3) vitamin B7 and mixtures thereof.

One embodiment of the invention involves adjusting, e.g. increasing a B vitamin concentration in the liquid nutrient medium above the cellular requirements of carboxydotrophic acetogenic microorganisms. Increasing the levels of vitamins B1 and B5, two essential B vitamins for the metabolism of Clostridium autoethanogenum has the effect of increasing the production of 2,3-BDO. These vitamins have been identified as key co-factors for enzymes involved in the biosynthesis of intermediates in 2,3-BDO production, including acetyl CoA, pyruvate and acetolactate. The role of B vitamins as co-factors is illustrated in FIG. 1.

It is taught in the art that carboxydotrophic microorganisms, such as Clostridium ljungdahlii, require 50 µg/g biomass produced of vitamin B5 for growth (for example, WO 2002/08438). It has been demonstrated that by increasing the concentration of either vitamin B5 or B1 in the liquid nutrient media from about 2 to about 80 times (or more) above cellular requirement the production of pyruvate-derived products is increased. In particular embodiments, the concentration of vitamin B5 in the liquid nutrient medium can be increased from about 2 to about 80 or from about 2 to about 60 or from 2 to about 40 or from about 2 to about 30 or from about 2 to about 20 or from about 2 to about 10 or from about 4 to about 80 or from about 4 to about 60 or from about 4 to about 40 or from about 4 to about 30 or from about 4 to about 20 or from about 4 to about 15 or form about 4 to about 10 or from about 8 to about 80 or from about 8 to about 60 or from about 8 to about 40 or from about 8 to about 30 or from about 8 to about 20 or from about 15 to about 80 or from about 15 to about 60 or from 15 to about 40 or from 15 to about 30 or from about 25 to about 80 or from about 25 to about 60 or from about 25 to about 40 or from about 80 or from about 40 to about 60 times the cellular requirement. In terms of actual concentration a broad embodiment of the invention is one in which the vitamin B5 concentration in the liquid nutrient medium is from about 100 µg/g biomass produced to about 4000 µg/g biomass produced. In particular embodiments the concentration of vitamin B5 in the liquid nutrient medium is from about 100 to about 3000 or from 100 to about 2000 or from about 100 to about 1500 or from 100 to about 1000 or from 200 to about 4000 or from 200 to about 3000 or from 200 to about 2000 or from 200 to about 1500 or from 200 to about 1000 or from 400 to about 4000 or from 400 to about 3000 or from about 400 to about 2000 or from 400 to about 1500 or from 600 to about 4000 or from 600 to about 3000 or from 600 to about 2000 µg/g biomass produced.

In the case of vitamin B1, a broad embodiment of the invention is one where the vitamin B1 concentration in the liquid nutrient medium is increased from about 2 to about 30 or from about 2 to about 20 or from about 2 to about 10 or from about 4 to about 30 or from about 4 to about 20 or from about 4 to about 15 or from about 6 to about 30 or from about 6 to about 20 or from about 6 to about 15 or from about 8 to about 30 or from about 8 to about 20 or from about 10 to about 30 or from about 15 to about 30 or from about 20 to about 30 times the cellular requirement. In terms of actual concentration a broad embodiment of the invention is one in which the vitamin B1 concentration in the liquid nutrient medium is from about 20 to about 500 µg/g biomass produced. In particular embodiments the concentration of vitamin B1 in the liquid nutrient medium can vary from about 20 to about 400 or from about 20 to about 300 or form about 20 to about 200 or from about 40 to about 500 or from 40 to about 300 or from about 40 to about 200 or from about 60 to about 500 or from about 60 to about 400 or from about 60 to about 300 or form about 60 to about 200 or from about 100 to about 500 or from about 100 to about 400 or from about 100 to about 300 or from about 100 to about 200 µg/g biomass produced.

The inventors have demonstrated that increasing the concentration of vitamin B7 in the liquid nutrient medium results in increased 2,3-BDO production. This increase is due to increasing the availability of metabolic precursors. Vitamin B7 is required for activity of acetyl-CoA carboxylase and pyruvate carboxylase. Surprisingly the inventors have shown that by increasing the concentration of vitamin B7, such that B7 is provided in excess to cellular requirements of the microorganism, the production of 2,3-BDO is increased. Interestingly it has been demonstrated that the increase in B7 does not affect biomass production or CO uptake. In particular embodiments, the concentration of vitamin B7 in the liquid nutrient medium can be increased from about 2 to about 30 or from about 2 to about 20 or from 2 to about 15 or from about 2 to about 10 or from about 4 to about 20 times or from about 4 to about 15 or form about 4 to about 10 times the cellular requirement. In particular embodiments, the concentration of vitamin B7 in the liquid nutrient medium can vary from about 100 to 4000 or 100 to about 3000 or from 100 to about 2000 or from about 100 to about 1500 or from about 100 to about 1000 or from 200 to about 4000 or from 200 to about 3000 or from 200 to about 2000 or from 200 to about 1500 or from 200 to about 1000 or from 400 to about 4000 or from 400 to about 3000 or from about 400 to about 2000 or from 400 to about 1500 or from 600 to about 4000 or from 600 to about 3000 or from 600 to about 2000 µg/g biomass produced. In particular embodiments, increasing the concentration of vitamin B7 in the liquid nutrient medium improves the ratio of ethanol:2,3-BDO in favour of 2,3-BDO.

When any of the B vitamins was increased above the cellular requirement (as described above) the production and the concentration of pyruvate derived products, e.g. 2,3-BDO increased while the production or concentration of Acetyl coA derived products, e.g. ethanol was virtually not affected. Therefore, it is another aspect of the invention that the ratio of ethanol:2,3-BDO can be controlled to a certain value or range by adjusting the concentration of at least one of the B vitamins within the ranges set forth above. Accordingly, the ethanol:2,3-BDO ratio can be varied from about 4:1 to about 1:2 or from about 4:1 to about 1:1 or from 4:1 to about 2:1 or from about 3:1 to about 1:2 or from about 3:1 to about 1:1 or from about 3:1 to about 2:1 with the lower ratios (higher 2,3-BDO concentration/production) being achieved at higher B vitamin concentrations.

In particular embodiments, the at least one nutrient concentration in the liquid nutrient medium is increased above the cellular requirement at the beginning of the fermentation process and maintained at the excess concentration, i.e. above the cellular requirement throughout the process. Alternatively, the fermentation process is started using a liquid nutrient medium comprising standard concentrations of nutrients, and the concentration of nutrients is increased to a desired concentration above the cellular requirement at a specific time point during the fermentation process. It has also been discovered that when the concentration of the at least one nutrient is decreased from the concentration above the cellular requirement to that of the cellular requirement or somewhere in between, the production of 2,3-BDO is reduced. In the case where the concentration is reduced to the cellular requirement concentration, the 2,3-BDO production returns to substantially the initial production. Therefore, the current invention allows one to tailor the production of pyruvate derived products, e.g. 2,3-BDO and Acetyl coA derived products, e.g. ethanol during an entire fermentation process or during various time periods. This is especially important if the products of the fermentation, e.g. 2,3-BDO and ethanol are used to produce other chemical such as butadiene or fuels, e.g. jet fuel.

Fermentation of gaseous substrates comprising CO by acetogenic carboxydotrophic microorganisms leads to the production of ethanol as a primary fermentation product at relatively high concentrations, and production of relatively low concentrations of 2,3-BDO. There is, therefore, provided a method for decreasing the ratio of ethanol:2,3-butanediol, i.e. increasing 2,3-BDO concentration produced by a microbial fermentation of a gaseous CO substrate by increasing the concentration of at least one of vitamin B1, vitamin B5 or vitamin B7 above their cellular requirement. The concentration of vitamin B1, vitamin B5 and vitamin B7 can be varied individually or in any combination. That is, vitamin B5 alone can be increased, vitamin B1 alone can be increased, etc. Alternatively, vitamin B5 and vitamin B1 can be increased while keeping vitamin B7 constant; vitamin B7 and vitamin B5 can be increased while keeping vitamin B1 constant or vitamin B1 and B7 can be increased while keeping vitamin B5 constant. In a yet another embodiment, all three of the B vitamins are increased above their cellular requirements.

In particular embodiments, the concentration of at least one of the above nutrients in the liquid nutrient medium is increased above the cellular requirement such that the microorganism produces 2,3-butanediol at a production rate of greater than 5 g/L per day or greater than 10 g/L per day or greater than 20 g/L per day.

In particular embodiments, the microorganism is capable of utilising CO to produce ethanol at a production rate of greater than 10 g/L per day or greater than 15 g/L per day or greater than 20 g/L per day or greater than 30 g/L per day or greater 40 g/L per day.

In particular embodiments of the method, the fermentation process is a continuous process. In one embodiment of the method, a two bioreactor system is used for the production of 2,3-butanediol and ethanol. In one embodiment, a multiple reactor system is used.

The fermentation may be carried out in any suitable bioreactor, such as an immobilised cell reactor, a gas-lift reactor, a bubble column reactor (BCR), a membrane reactor, such as a Hollow Fibre Membrane Bioreactor (HFMBR) or a trickle bed reactor (TBR). Also, in some embodiments of the invention, the bioreactor may comprise a first growth reactor in which the micro-organisms are cultured, and a second fermentation reactor, to which fermentation broth from the growth reactor may be fed and in which most of the fermentation product (e.g. ethanol and acetate) may be produced. The bioreactor of the present invention is adapted to receive a gaseous substrate selected from the group consisting of CO, $CO_2$, $H_2$ and mixtures thereof.

The acetogenic carboxydotrophic bacterium is selected from *Clostridium*, *Moorella*, *Oxobacter*, *Peptostreptococcus*, *Acetobacterium*, *Eubacterium*, or *Butyribacterium*. In various embodiments, the microorganism is selected from the group consisting of *Clostridium autoethanogenum*, *Clostridium ljungdahli*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrphoicum*, *Acetobacterium woodii*, *Alkalibaculum bacchi*, *Blautia producta*, *Eubacterium limosum*, *Moorella thermoacetica*, *Sporomusa ovata*, *Sporomusa silvacetica*, *Sporomusa sphaeroides*, *Oxobacter pfennigii* and *Thermoanaerobacter kiuvi*.

In particular embodiments, the microorganism is *Clostridium autoethanogenum* or *Clostridium ljungdahlii*. In one particular embodiment, the microorganism is *Clostridium autoethanogenum*. In a particular embodiment, the *Clostridium autoethanogenum* is a *Clostridium autoethanogenum* having the identifying characteristics of the strain deposited at the German Resource Centre for Biological Material (DSMZ and having the accession number DSM10061 or DSM19630 or DSM 23693.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

Fermentation

As stated above examples of bacterium that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al., Archives of Microbiology 161: pp 345-351). Other suitable bacteria include those of the genus *Moorella*, including *Moorella* sp HUC22-1 (Sakai et al., Biotechnology Letters 29: pp 1607-1612), and those of the genus *Carboxydothermus* (Svetlichny, V. A., et al. (1991), Systematic and Applied Microbiology 14: 254-260). The disclosures of each of these publications are incorporated herein by reference. In addition, other carboxydotrophic anaerobic bacteria can be used in the processes of the invention by a person of skill in the art. It will also be appreciated upon consideration of the instant disclosure that a mixed culture of two or more bacteria may be used in processes of the present invention.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

In one embodiment, the microorganism is selected from the group of carboxydotrophic Clostridia comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum*. In a further embodiment, the microorganism is from the cluster of carboxydotrophic Clostridia comprising the species *C. autoethanogenum, C. ljungdahlii*, and *C. ragsdalei* and related isolates. These include but are not limited to strains *C. autoethanogenum* JAI-1T (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETCT (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), *C. ragsdalei* P11T (ATCC BAA-622) (WO 2008/028055), related isolates such as "*C. coskatii*" (US20110229947) and "*Clostridium* sp." (Tyurin & Kiriukhin, 2012), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of the above-referenced cluster have a similar morphology and size (logarithmic growing cells are between 0.5-0.7×3-5 µm), are mesophilic (optimal growth temperature between 30-37° C.) and strictly anaerobe (Abrini et al., 1994; Tanner et al., 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions (Abrini et al., 1994; Köpke et al., 2011; Tanner et al., 1993) (WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke et al., 2011). Also reduction of carboxylic acids into their corresponding alcohols has been shown in a range of these organisms (Perez, Richter, Loftus, & Angenent, 2012). These traits are therefore not specific to one organism like *C. autoethanogenum* or *C. ljungdahlii*, but rather general traits for carboxydotrophic, ethanol-synthesizing Clostridia and it can be anticipated that mechanism work similar across these strains, although there may be differences in performance (Perez et al., 2012)

The fermentation may be carried out in any suitable bioreactor. In some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

The CO Containing Substrate

A substrate comprising carbon monoxide, preferably a gaseous substrate comprising carbon monoxide, is used in the fermentation reaction of the invention. The gaseous substrate may be a waste gas obtained as a by-product of an industrial process, or from some other source such as from combustion engine (for example automobile) exhaust fumes. In certain embodiments, the industrial process is selected from the group consisting of ferrous metal products manufacturing, such as conducted in a steel mill, non-ferrous products manufacturing, petroleum refining processes, gasification of coal, electric power production, carbon black production, ammonia production, methanol production and coke manufacturing. In these embodiments, the CO-containing gas is captured from the industrial process before it is emitted into the atmosphere, using any convenient method.

In a specific embodiment, the substrate comprising CO is derived from the steel manufacturing process. In the steel making process, iron ore is crushed and pulverised, subjected to pre-treatments such as sintering or pelletizing, and then passed to a blast furnace (BF), where it is smelted. In the smelting process, coke serves as the source of carbon, which works as a reducing agent to reduce the iron ore. Coke acts as the heat source for heating and melting the materials. The hot metal is decarburised in a basic oxygen furnace (BOF) by injecting a high-velocity jet of pure oxygen against the surface of the hot metal. The oxygen reacts directly with carbon in the hot metal to produce carbon monoxide (CO). Thus, a gas stream with a high CO content is exhausted from the BOF. According to certain embodiments of the invention, this stream is used to feed one or more fermentation reactions. However, as would be apparent to one of skill in the art, CO may be produced elsewhere within the steel making process, and according to various embodiments of the invention, such alternative sources may be used instead of or in combination with exhaust gases from the BOF. Depending on the source (i.e., the particular stage within the steel making process), the CO content of the gases exhausted thereby may vary. Also, there may be periods when there are breaks in one or more of such streams, particularly in batch processing plants.

Typically, streams exhausted from the steel mill decarburisation process comprise a high concentration of CO and low concentrations of $H_2$. While such streams can be directly passed to the bioreactor with little or no further treatment, it may be desirable to optimise the composition of the substrate stream in order to achieve higher efficiency of alcohol production and/or overall carbon capture. For example, the concentration of $H_2$ in the substrate stream may be increased before the stream is passed to the bioreactor.

According to particular embodiments of the invention, streams from two or more sources can be combined and/or blended to produce a desirable and/or optimised substrate stream. For example, a stream comprising a high concentration of CO, such as the exhaust from a steel mill converter, can be combined with a stream comprising high concentrations of $H_2$, such as the off-gas from a steel mill coke oven.

An early stage of the steel making process typically involves the reduction of iron ore using coke. Coke is a solid carbon fuel source used to melt and reduce iron ore and is typically produced on-site at a steel mill. In the coke-making process, bituminous coal is fed into a series of ovens, which are sealed and heated at high temperatures in the absence of oxygen, typically in cycles lasting 14 to 36 hours. The solid carbon remaining in the oven is coke. It is taken to the quench tower, where it is cooled with a watery spray or by circulating an inert gas (nitrogen), then screened and sent to the blast furnace.

The volatile compounds produced during this process are generally processed to remove tar, ammonia, naphthalene, phenol, light oils and sulphur before the gas is used as fuel to heat ovens. Gas produced as a result of coke production typically has a high $H_2$ content (typical composition: 55% $H_2$, 25% $CH_4$, 6% CO, 3% $N_2$, 2% other hydrocarbons). As such, at least a portion of the coke oven gas may be diverted to the fermentation process for blending with a stream comprising CO, to improve alcohol productivity and/or overall carbon capture. It may be necessary to treat the coke oven gas prior to passing it to the fermenter to remove by-products that may be toxic to the culture.

In other embodiments, the substrate comprising CO can be derived from the steam reforming of hydrocarbons. Hydrocarbons, such as natural gas hydrocarbons can be reformed at high temperature to yield CO and $H_2$ according to the following:

$$C_nH_m + nH_2O \rightarrow nCO + (m/2+n)H_2$$

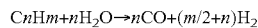

By way of example, steam methane reforming involves reacting steam with methane to produce CO and $H_2$ at elevated temperature (700-1100° C.) in the presence of a nickel catalyst. The resulting stream (comprising 1 mol CO and 3 mol $H_2$ for every mol $CH_4$ converted) can be passed directly to the fermenter or blended with a substrate stream from another source to increase ethanol productivity and/or overall carbon capture in a fermentation process. Alcohols such as methanol can also be reformed to produce $CO_2$ and H2 that may be used in a similar manner.

In some embodiments, the CO-containing gaseous substrate may be sourced from the gasification of organic matter such as methane, ethane, propane, coal, natural gas, crude oil, low value residues from oil refinery (including petroleum coke or petcoke), solid municipal waste or biomass. Biomass includes by-products obtained during the extraction and processing of foodstuffs, such as sugar from sugarcane, or starch from maize or grains, or non-food biomass waste generated by the forestry industry. Any of these carbonaceous materials can be gasified, i.e. partially combusted with oxygen, to produce synthesis gas (syngas comprising significant amounts of $H_2$ and CO). Gasification processes typically produce a synthesis gas with a molar ratio of $H_2$ to CO of about 0.4:1 to 1.2:1, together with lesser amounts of $CO_2$, $H_2S$, methane and other inert substances. The ratio of the gas produced can be varied by means known in the art and are described in detail in WO200701616. However, by way of example, the following gasifier conditions can be altered to adjust the CO:$H_2$ product ratio: feedstock composition (particularly C:H ratio), operating pressure, temperature profile (influencing quench of product mix) and oxidant employed (air, oxygen enriched air, pure $O_2$ or steam; wherein steam tends to result in higher CO:$H_2$ ratios). Accordingly, the operating conditions of the gasifier can be adjusted to provide a substrate stream with a desirable composition for fermentation or blending with one or more other streams to provide an optimised or desirable composition for increased alcohol productivity and/or overall carbon capture in a fermentation process.

The reforming of gases or gasification of biomass e.g. production of syngas, to produce CO containing streams are described in US Patent Application Publication No. US2013/0210096A1; US2013/0203143A1; US2013/0045517A1 and U.S. Pat. No. 8,376,736 all of which are incorporated by reference in their entirety.

Depending on the composition of the gaseous substrate comprising carbon monoxide, it may also be desirable to treat it to remove any undesired impurities, such as dust particles before introducing it to the fermentation. For example, the gaseous substrate may be filtered or scrubbed using known methods.

The CO-containing substrate will typically contain a major proportion of CO, such as at least about 15% to about 100% CO by volume, from about 15% to about 70% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present. In some embodiments, the substrate comprises from about 5% to about 70% CO.

Regardless of the source of the gaseous stream comprising CO, it will usually contain a number of other gases such as $CO_2$, $H_2$, $N_2$, $CH_4$, etc. For example $CO_2$ may be present in a concentration from about 1% to about 80% by volume, or about 1% to about 30% by volume or about 5% to about 30%. In a broad embodiment, the substrate which is passed to the bioreactor will typically have concentrations of about 20 to about 80% CO, from about 0 to about 30% $H_2$ and from about 0 to about 40% $CO_2$.

Typically, the carbon monoxide will be added to the fermentation reaction in a gaseous state. However, the invention should not be considered to be limited to addition of the substrate in this state. For example, the carbon monoxide could be provided in a liquid. For example, a liquid may be saturated with a carbon monoxide containing gas and then that liquid added to a bioreactor. This may be achieved using standard methodology. By way of example, a microbubble dispersion generator (Hensirisak et. al. Scale-up of microbubble dispersion generator for aerobic fermentation; *Applied Biochemistry and Biotechnology* Volume 101, Number 3/October, 2002) could be used.

In addition, it is often desirable to increase the CO concentration of a substrate stream (or CO partial pressure in a gaseous substrate) and thus increase the efficiency of fermentation reactions where CO is a substrate. Increasing CO partial pressure in a gaseous substrate increases CO mass transfer into a fermentation media. The composition of gas streams used to feed a fermentation reaction can have a significant impact on the efficiency and/or costs of that reaction. For example, $O_2$ may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

The removal of unwanted gaseous components from the substrate stream can be carried by conventional techniques such as cryogenic fractionation, molecular sieving, adsorption, pressure swing adsorption, or absorption. Whatever process is used, gas separation can be performed to isolate at least a portion of one or more of the following components: $H_2$, $O_2$, $CO_2$ and CO, from the gas stream. Additionally or alternatively, gas separation according to embodiments of the invention may be used to remove one or more portions from the gas stream (e.g. $N_2$, $O_2$) so that the remainder may be more efficiently used, such as in the bioreactor.

Adsorption is the accumulation of gases, liquids or solutes on the surface of a solid or liquid. Absorption is the process by which one substance, such as a solid or liquid, takes up another substance, such as a liquid or gas, through minute pores or spaces between its molecules.

Pressure swing adsorption (PSA) is an adiabatic process which may be used for the purification of gases to remove accompanying impurities by adsorption through suitable adsorbents in fixed beds contained in pressure vessels under high pressure. Regeneration of adsorbents is accomplished by countercurrent depressurization and by purging at low pressure with previously recovered near product quality gas. To obtain a continuous flow of product, preferably at least two adsorbers are provided, such that at least one adsorber is receiving a gas stream (such as a waste/exhaust/biogas gas stream) and actually produces a product of desired purity. Simultaneously, the subsequent steps of depressurization, purging and repressurization back to the adsorption pressure are executed by the other adsorber(s). Common adsorbents may readily be selected by one of skill in the art dependent on the type of impurity to be adsorbed and removed. Suitable adsorbents include zeolitic molecular sieves, activated carbon, silica gel or activated alumina. Combinations of adsorbent beds may be used on top of one another, thereby dividing the adsorber contents into a number of distinct zones. Pressure swing adsorption involves a pendulating swing in parameters such as pressure, temperature, flow and composition of gaseous and adsorbed phase.

Purification or separation of gases using PSA normally takes place at near ambient feed gas temperatures, whereby the components to be removed are selectively adsorbed. Adsorption should ideally be sufficiently reversible to enable regeneration of adsorbents at similar ambient temperature. PSA may be used for treatment and/or purification of most common gases including CO, $CO_2$ and $H_2$. Examples of Pressure Swing Adsorption techniques are described in detail in Ruthven, Douglas M. et al., 1993 Pressure Swing Adsorption, John Wiley and Sons.

A molecular sieve is a material containing tiny pores of a precise and uniform size that is used as an adsorbent for gases and liquids. Molecules that are small enough to pass through the pores are adsorbed while larger molecules are not. A molecular sieve is similar to a common filter but operates on a molecular level. Molecular sieves often consist of aluminosilicate minerals, clays, porous glasses, microporous charcoals, zeolites, active carbons, or synthetic compounds that have open structures through which small molecules, such as nitrogen and water, can diffuse. Methods for regeneration of molecular sieves include pressure changing (e.g. in oxygen concentrators) and heating and purging with a carrier gas.

Membranes may be used, for example, to separate hydrogen from gases like nitrogen and methane, to recover hydrogen, to separate methane from biogas, or to remove water vapour, $CO_2$, $H_2S$ or volatile organic liquids. Different membranes, including porous and non-porous membranes, may be selected to serve the desired purpose as would be apparent to one of skill in the art upon consideration of the instant disclosure. For example, a Palladium membrane permits transport solely of $H_2$. In a particular embodiment, $CO_2$ can be separated from a stream, using a $CO_2$ permeable membrane. The $CO_2$ separated from the stream can be passed to a $CO_2$ remover such as the gasifier discussed previously.

Cryogenic fractionation involves compressing the gas stream and cooling it to a temperature low enough to allow separation by distillation. It may be used, for example, to remove $CO_2$. Certain components (e.g. water) are typically removed from the stream prior to performing cryogenic fractionation.

The same techniques can also be used to remove oxygen from a gaseous stream to produce CO and/or $CO_2$-rich anaerobic streams. In addition, oxygen can be removed biologically, by, for instance, passing the combustion exhaust gas into a sealed fermenter containing facultative aerobic micro-organisms, a reduced carbon substrate, and the necessary nutrients for the micro-organisms. The facultative aerobic micro-organisms can consume oxygen to create CO and/or $CO_2$-rich anaerobic streams.

Alternative methods for separating or removing $O_2$ from a gaseous stream are also well known in the art. However, by way of example, oxygen can be simply reduced and/or removed using hot copper or a catalytic converter.

Tailoring the gas separation process to a particular source of gas can make an otherwise non-commercially viable bioconversion process commercially viable. For example, with appropriate separation of CO from a car exhaust stream, a usable energy source may be obtained from the stream and unwanted gas emissions can be reduced. According to one embodiment of the invention, the gaseous substrate comprises Syngas containing CO and $H_2$, and gas separation is performed to remove hydrogen from the stream so that it may be isolated and used as a fuel outside of the fermentation process. The CO may be used to feed the fermentation reaction.

The pH of the fermentation broth used in the fermentation process may be adjusted as required. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO utilising *Clostridium autoethanogenum*, the pH may be adjusted to approximately 4.5 to 6.5. Further examples include pH 5.5 to 6.5 using *Moorella thermoacetica* for the production of acetic acid, pH 4.5 to 6.5 using *Clostridium acetobutylicum* for the production of butanol, and pH 7 using *Carboxydothermus hygrogenaformans* for the production of hydrogen. Those skilled in the art will be aware of suitable means for maintaining the bioreactor at the required pH. However, by way of example, aqueous bases such as NaOH and aqueous acids such as $H_2SO_4$ can be used to raise and lower the pH of the fermentation medium and maintain the desired pH.

An additional benefit of the invention is that, because there is no or only minimal scrubbing and/or other treatment processes performed on the waste gases prior to their use in a fermentation reaction, the gases will contain additional material resulting from the industrial process, which additional material may be used, at least in part, as a feedstock for the fermentation reaction.

Blending of Streams

It may be desirable to blend a reformed substrate stream comprising CO and $H_2$ with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

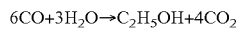

However, in the presence of $H_2$, the overall conversion can be as follows:

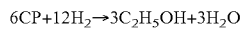

Accordingly, streams with high CO content can be blended with reformed substrate streams comprising CO and $H_2$ to increase the CO:$H_2$ ratio to optimise fermentation efficiency. By way of example, industrial waste streams, such as off-gas from a steel mill have a high CO content, but include minimal or no $H_2$. As such, it can be desirable to blend one or more streams comprising CO and $H_2$ with the waste stream comprising CO, prior to providing the blended substrate stream to the fermenter. The overall efficiency, alcohol productivity and/or overall carbon capture of the fermentation will be dependent on the stoichiometry of the CO and $H_2$ in the blended stream. However, in particular embodiments the blended stream may substantially comprise CO and $H_2$ in the following molar ratios: 20:1, 10:1, 5:1, 3:1, 2:1, 1:1 or 1:2.

In addition, it may be desirable to provide CO and $H_2$ in particular ratios at different stages of the fermentation. For example, substrate streams with a relatively high $H_2$ content (such as 1:2 CO:$H_2$) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the $H_2$ concentration may be greater or equal to zero).

Blending of streams may also have further advantages, particularly in instances where a waste stream comprising CO is intermittent in nature. For example, an intermittent waste stream comprising CO may be blended with a substantially continuous reformed substrate stream comprising CO and $H_2$ and provided to the fermenter. In particular embodiments of the invention, the composition and flow rate of the substantially continuous blended stream may be varied in accordance with the intermittent stream in order to maintain provision of a substrate stream of substantially continuous composition and flow rate to the fermenter.

Media

It will be appreciated that for growth of the one or more microorganisms and substrate to ethanol and/or acetate fermentation to occur, in addition to the substrate, a suitable nutrient medium will need to be fed to the bioreactor. A nutrient medium will contain components, such as vitamins and minerals, sufficient to permit growth of the microorganism used. By way of example only, anaerobic media suitable for the growth of Clostridium autoethanogenum are known in the art, as described for example by Abrini et al (Clostridium autoethanogenum, sp. Nov., An Anaerobic Bacterium That Produces Ethanol From Carbon Monoxide; Arch. Microbiol., 161: 345-351 (1994)). The "Examples" section herein after provides further examples of suitable media.

The Bioreactor

The fermentation may be carried out in any suitable bioreactor, such as an immobilised cell reactor, a gas-lift reactor, a bubble column reactor (BCR), a membrane reactor, such as a Hollow Fibre Membrane Bioreactor (HFM BR) or a trickle bed reactor (TBR). Also, in some embodiments of the invention, the bioreactor may comprise a first growth reactor in which the micro-organisms are cultured, and a second fermentation reactor, to which fermentation broth from the growth reactor may be fed and in which most of the fermentation product (e.g. ethanol and acetate) may be produced. The bioreactor of the present invention is adapted to receive a $CO_2$, $H_2$ and optionally CO containing substrate.

Fermentation Conditions

Processes for the production of ethanol and other alcohols from gaseous substrates are known. Exemplary processes include those described for example in WO2007/117157, WO2008/115080, WO2009/022925, WO2009/064200, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

The fermentation should desirably be carried out under appropriate conditions for the substrate to ethanol and/or acetate fermentation to occur. Reaction conditions that should be considered include temperature, pressure, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in general, it is preferred that the fermentation be performed at a pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-product conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-product fermentation at elevated pressures have also been described elsewhere. For example, WO 02/08438 describes gas-to-ethanol fermentations performed under pressures of 200 kPag (29 psig) and 520 kPag (75 psig), giving ethanol productivities of 150 g/l/day and 369 g/l/day respectively. However, example fermentations performed using similar media and input gas compositions at atmospheric pressure were found to produce between 10 and 20 times less ethanol per litre per day. Therefore, the fermentation process can be carried out from atmospheric pressure (0 kPag) to about 600 kPag.

Examples of fermentation conditions suitable for anaerobic fermentation of a substrate comprising CO are detailed in WO2007/117157, WO2008/115080, WO2009/022925 and WO2009/064200. It is recognised the fermentation conditions reported therein can be readily modified in accordance with the methods of the instant invention.

Fermentation Products

Both the pyruvate derived products and the Acetyl coA derived products can be used as produced or they can be used in the production of other chemicals such as the production of plastics, pharmaceuticals and agrochemicals. In one embodiment, the fermentation product is used to produce gasoline range hydrocarbons (about 8 carbon), diesel hydrocarbons (about 12 carbon) or jet fuel hydrocarbons (about 12 carbon). Ethanol and acetate can then be reacted to together to produce chemical products including esters. In one embodiment of the invention the ethanol and acetate produced by fermentation are reacted together to produce ethyl acetate. Ethyl acetate may be of value for a host of other processes such as the production of solvents including surface coating and thinners as well as in the manufacture of pharmaceuticals and flavours and essences.

In the case of 2,3-BDO it can be converted into an eight-carbon dimer which can be used as aviation fuel. The 2,3-BDO can also be converted to a compound selected from the group consisting of butene(s), butadiene, methyl ethyl ketone (MEK) and mixtures thereof. The conversion of 2,3-BDO to various chemical compounds is disclosed in U.S. Pat. No. 8,658,408.

The invention also provides that at least a portion of a hydrocarbon product produced by the fermentation is reused in the steam reforming process. This may be performed because hydrocarbons other than $CH_4$ are able to react with steam over a catalyst to produce $H_2$ and CO. In a particular embodiment, ethanol is recycled to be used as a feedstock for the steam reforming process. In a further embodiment, the hydrocarbon feedstock and/or product is passed through a prereformer prior to being used in the steam reforming process. Passing through a prereformer partially completes the steam reforming step of the steam reforming process which can increase the efficiency of hydrogen production and reduce the required capacity of the steam reforming furnace.

Product Recovery

The products of the fermentation reaction can be recovered using known methods. Exemplary methods include those described in WO07/117157, WO08/115080, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non-volatile and is recovered for re-use in the fermentation.

Acetate, which may be produced as a by-product in the fermentation reaction, may also be

TABLE 1

Fermentation media
Media

| Component | Concentration (mM/L) |
|---|---|
| $MgCl_2$ 6 $H_2O$ | 2 |
| NaCl | 2 |
| $CaCl_2$ 6 $H_2O$ | 2 |
| KCl | 25 |
| $H_3PO_4$ 85% | 0.375 mL |
| Trace metal | 7.5 mL |
| B-vitamins | 20 mL |

| Trace metal composition | Final concentration in the media (µmol/L) | Concentration (mM/L) 200 x stock solution |
|---|---|---|
| $FeCl_2$ $4H_2O$ | 150 | 20 |
| $CoCl_2$ $6H_2O$ | 7.5 | 1 |
| $ZnCl_2$ | 7.5 | 1 |
| $H_3BO_3$ | 3 | 0.4 |
| $MnCl_2$ $4H_2O$ | 3 | 0.4 |
| $Na_2MoO_4$ $2H_2O$ | 3 | 0.4 |
| $NiCl_2$ $6H_2O$ | 3 | 0.4 |
| $Na_2WO_4$ $2H_2O$ | 3 | 0.4 |
| $Na_2SeO_3$ | 3 | 0.4 |

| Vitamin | Final concentration in the media (mg/L) | Concentration (mg/L) 100 x stock solution |
|---|---|---|
| Thiamine hydrocloride (B1) | 1 | 50 |
| Riboflavin (B2) | 1 | 50 |
| Nicotinic acid (B3) | 1 | 50 |
| Pantothenic acid (B5) | 1 | 50 |
| Pyridoxine hydrochloride (B6) | 0.2 | 10 |
| Biotin (B7) | 0.4 | 20 |
| Folic acid (B9) | 0.2 | 10 |
| 4-Aminobenzoic acid (PABA or B10) | 1 | 50 |
| Cyanocobalamin (B12) | 1 | 50 |
| Lipoic acid (Thiotic acid) | 1 | 50 |

Example 1

Effect of Increasing Vitamin B5 Concentration on 2,3-BDO Production

This experiment was carried out according to the general fermentation process described above. During the course of the fermentation experiment, gas flow and agitation were increased to minimize acetate and maximize ethanol production. Dilution rate and bacterial dilution rate were adjusted so that by day 5.0 these were 1.8 day$^{-1}$ and 0.85 day$^{-1}$, respectively. These values were maintained for the remainder of the fermentation. Between day 6.0-day 8.0 stable data was achieved with the B5 feed rate of 198 µg/g-cell produced. The results achieved during this stable period are summarised in Table 2.

TABLE 2

Results of fermentation with 198 µg/g-cell produced of vitamin B5

| Measure | Concentration |
| --- | --- |
| Biomass | 10.62 g/L |
| CO uptake | 8.4 mol/L/day |
| Ethanol | 18.69 g/L |
| Acetate | 7.75 g/L |
| 2,3-BDO | 4.8 g/L |
| Specific 2,3-BDO production rate | 0.81 g 2,3-BDO/g-biomass/day |
| Specific Ethanol production rate | 3.17 g ethanol/g-biomass/day |
| Ethanol:2,3-BDO ratio | 3.8:1 |

On day 8.1 the concentration of vitamin B5 in media was increased 10 fold with all other operational parameters remaining the same. During this time the biomass production rate dropped slightly so accordingly the vitamin B5 feed rate was increased just over tenfold to 2180 µg/g-cell produced. Following the increase in the vitamin B5 concentration, the specific 2,3-BDO production rate and concentration increased with other parameters remaining stable. The results are summarised below in Table 3.

TABLE 3

Results of fermentation with 2180 µg/g cell produced of vitamin B5

| Measure | Concentration |
| --- | --- |
| Biomass | 10.4 g/L |
| CO uptake | 8.0 mol/L/day |
| Ethanol | 19.49 g/L |
| 2,3-BDO | 7.0 g/L |
| Specific 2,3-BDO production rate | 1.32 g 2,3-BDO/g biomass/day |
| Specific Ethanol production rate | 3.3 g ethanol/g biomass/day |
| Ethanol:2,3-BDO ratio | 2.6:1 |

This is a surprising result as it is only the specific 2,3-BDO production rate and the concentration of 2,3-BDO that increases while the production rate of other metabolites, e.g. ethanol and biomass remains the same.

Example 3

Figure 2:
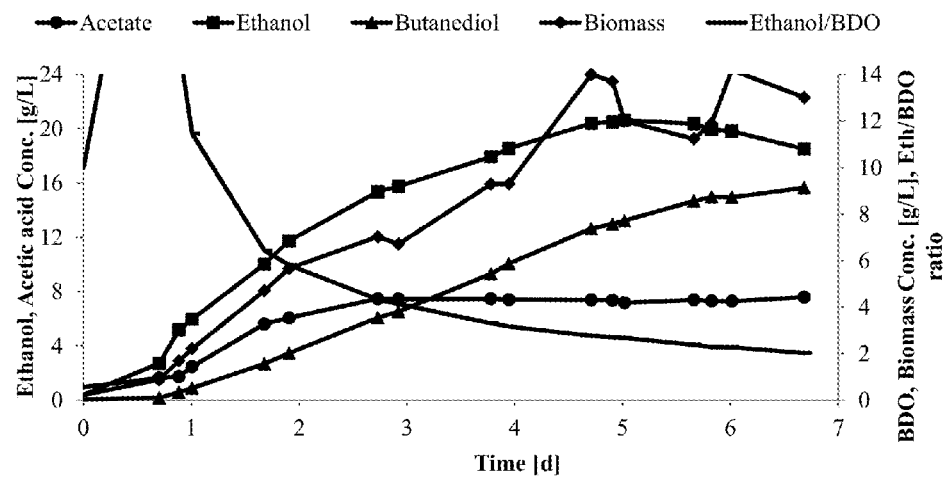
FIG. 2 presents plots of the metabolite and biomass concentrations from example 3
Figure 3:
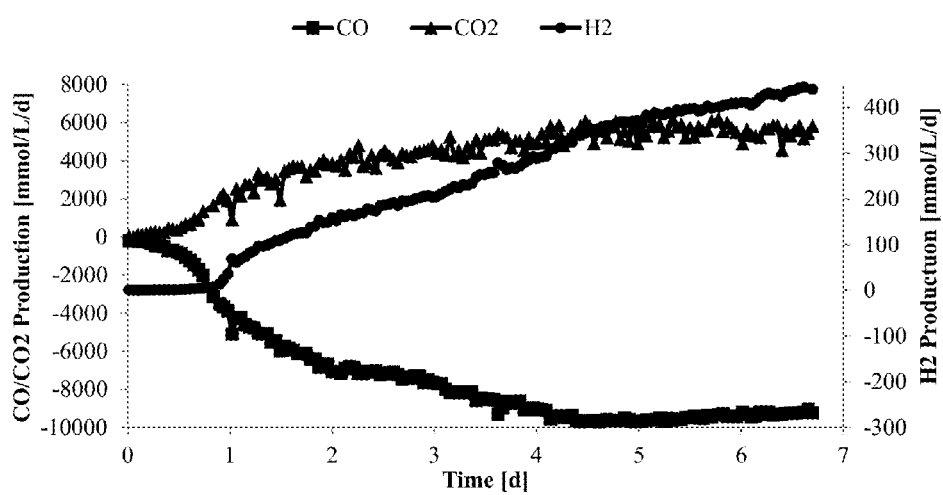
FIG. 3 presents plots showing the gas uptake profile for experiment 3.

Effect of Increasing Vitamin B5 from Start of Fermentation on 2,3-BDO Production The example above can be compared to results when excess B5 vitamin is present in the fermentation media throughout the fermentation. During this fermentation experiment gas and agitation were increased to minimize acetate and maximize ethanol production. Dilution rate and bacterial dilution rate were adjusted by day 4.0 to 1.7 day$^{-1}$ and 0.65 day$^{-1}$ respectively. In this case the 2,3-BDO concentration reached 9 g/L with an ethanol:2,3-BDO ratio of 2:1 (FIG. 2), and a CO uptake of 9.4 mol/L/day (FIG. 3). The feed rate of B5 vitamin throughout the fermentation was >2000 µg/g-cell produced. During day 6.0 to 7.0 as the biomass and 2,3-BDO production flattened out the feed rate of B5 vitamin was 2011 µg/g-cell produced. The specific 2,3-BDO production rate was 1.2 g/day per g-biomass, the specific ethanol production rate was 2.4 g/day per g-biomass.

Example 4

Effect of Increasing/Decreasing Vitamin B1 Concentration on 2,3-BDO Production

A fermentation was started using the general fermentation process with gas and agitation were increased to minimize acetate and maximize ethanol production. Dilution rate and bacterial dilution rate were adjusted by day 4.0 to 2.0 day-$^{1}$ and 1.2 day-1, respectively. These values were maintained for the remainder of the fermentation. Between day 10.0-day 14.0 stable data was achieved, the feed rate of B1 during this time was 303 µg/g-cell produced. The data achieved is summarized in Table 4.

TABLE 4

Results from excess vitamin B1 (303 µg/g cell produced)

| Measure | Concentration |
| --- | --- |
| Ethanol:2,3BDO ratio | 4.7:1 |
| 2,3-BDO | 3.4 g/L |
| Biomass | 5.79 g/L |
| Ethanol | 16.05 g/L |
| CO uptake | 8.0 mol/L/day |
| Specific 2,3-BDO production rate | 1.17 g 2,3-BDO/g biomass/day |
| Specific Ethanol production rate | 5.54 g ethanol/g biomass/day |

On day 14.1 the concentration of B1 in media was decreased to reduce the specific B1 feed rate with all other operational parameters being kept constant. Between day 14.1 to 22.0 there was a decrease in the production of 2,3-BDO and the ratio of ethanol:2,3BDO increased from 4.7:1 to 12:1. During this time the specific B1 feed rate decreased from 303 µg/g cell produced to 61 µg/g cell produced. The results are summarized in Table 5.

TABLE 5

Results from decreased vitamin B1 (61 µg/g cell produced)

| Measure | Concentration |
| --- | --- |
| Ethanol:2,3-BDO | 12:1 |
| 2,3-BDO titre | 1.6 g/L |
| Biomass | 6.75 g/L |
| Ethanol | 18.23 g/L |
| CO uptake | 8.0 mol/L/day |
| Specific 2,3-BDO production rate | 0.47 g 2,3-BDO/g biomass/day |
| Specific Ethanol production rate | 5.4 g ethanol/g biomass/day |

This is a surprising result because decreasing the B1 concentration decreased the production of 2,3-BDO while ethanol production was unaffected and while keeping CO uptake constant. It has been reported in the art that the limiting concentration of B1 for growth and acetate production is 6.5 µg/g cell produced. Therefore, supplying B1 well in excess of the minimum requirements for cell growth provides a way to control the production of 2,3-BDO and the ratio of ethanol:2,3-BDO.

Example 5

Effect of Increasing B7 Concentration on 2,3-BDO Production

In this example the impact of B7 on the production of 2,3-BDO was tested using a fermentation grown according to the general fermentation process. During the course of the fermentation gas and agitation were increased to minimize acetate and maximize ethanol production. Dilution rate and bacterial dilution rate were adjusted so that by day 8.0 these were 1.8 day$^{-1}$ and 0.75 day$^{-1}$ respectively. These values were maintained for the remainder of the fermentation. Stable data was achieved with the B7 feed rate at 90 µg/g cell produced. The results achieved at that time are summarised below;

TABLE 6

Results of fermentation with 90 µg/g cell produced of vitamin B7

| Measure | Concentration |
|---|---|
| Biomass | 9.42 g/L |
| CO uptake | 8.0 mol/L/day |
| Ethanol | 15.63 g/L |
| Acetate | 8.13 g/L |
| 2,3-BDO | 4.94 g/L |
| Specific 2,3-BDO production rate | 1.19 g 2,3-BDO/g biomass/day |
| Specific Ethanol production rate | 3.78 g ethanol/g biomass/day |
| Ethanol:2,3-BDO ratio | 3.2:1 |

On day 8.69 the concentration of B7 in media was increased 10 fold with all other operational parameters being kept constant. During this time the biomass production rate remained stable so the B7 feed rate was increased over tenfold to 980 µg/g cell produced. Following the increase in the B7 feed the specific 2,3-BDO production rate and the concentration of 2,3-BDO increased. The data obtained from days 13-14 are summarised below;

TABLE 7

Results of fermentation with 980 µg/g cell produced of vitamin B7

| Measure | Concentration |
|---|---|
| Biomass | 9.23 g/L |
| CO uptake | 7.6 mol/L/day |
| Ethanol | 14.92 g/L |
| 2,3-BDO | 7.34 g/L |
| Specific 2,3-BDO production rate | 1.97 g 2,3-BDO/g biomass/day |
| Specific Ethanol production rate | 3.85 g ethanol/g biomass/day |
| Ethanol:2,3-BDO ratio | 1.91:1 |

As the 2,3-BDO concentration was reaching a peak (day 14.04) the B7 in the media was reduced 10 fold such that the specific B7 feed rate was reduced back to 90 µg/g cell produced. The data for the variables measured were observed to be very close to those values observed before the increase in B7 concentration and are summarized below.

TABLE 8

Results of fermentation when vitamin B7 concentration was reduced to 90 µg/g cell produced

| Measure | Concentration |
|---|---|
| Biomass | 10.53 g/L |
| CO uptake | 7.6 mol/L/day |
| Ethanol | 15.70 g/L |
| 2,3-BDO | 4.76 g/L |
| Specific 2,3-BDO production rate | 1.1 g 2,3-BDO/g biomass/day |
| Specific Ethanol production rate | 3.59 g ethanol/g biomass/day |
| Ethanol:2,3-BDO ratio | 3.3:1 |

Figure 4:
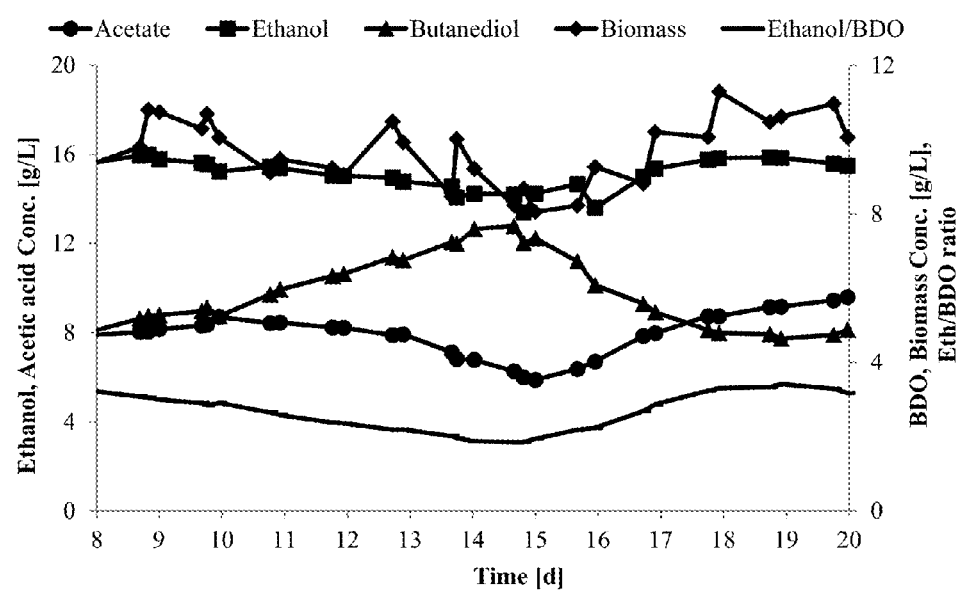
FIG. 4 presents plots of metabolite and biomass concentrations versus time for example 5.
Figure 5:
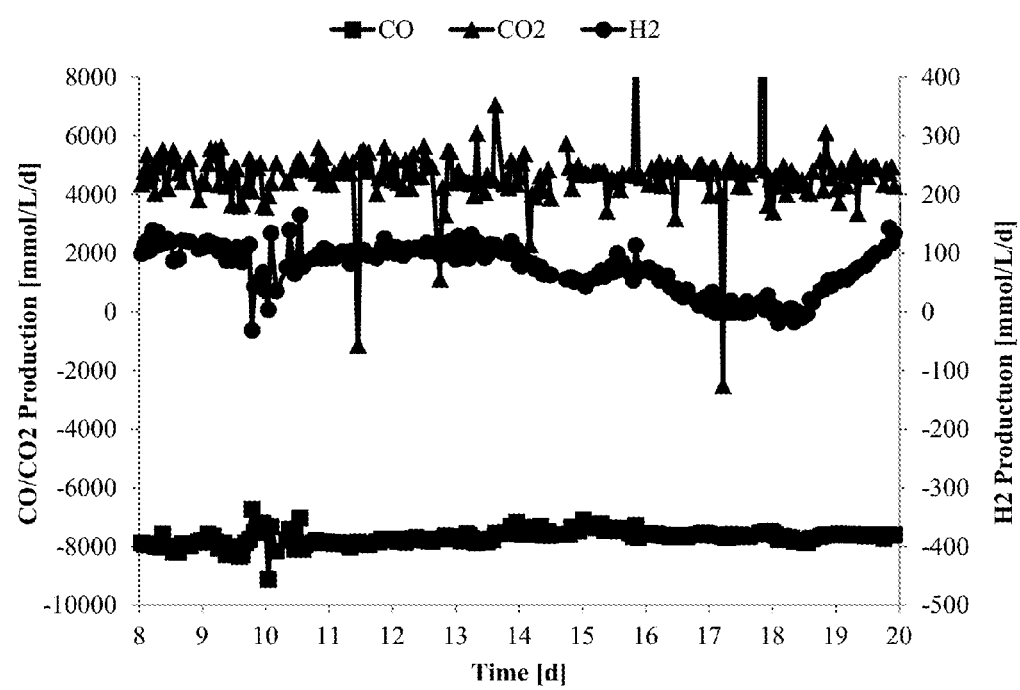
FIG. 5 presents plots showing gas uptake for example 5.

This is a surprising result as it is the specific 2,3-BDO production rate and the concentration of 2,3-BDO that increases rather than any other metabolite and or biomass. The results also show that the impact of increasing B7 is reversible and that increasing B7 does not impact the specific ethanol production rate. The results from the changes in B7 concentration are presented in FIGS. 4 and 5.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What is claimed is:

1. A method for the production of at least one product by microbial fermentation, the method comprising:
providing a gaseous substrate comprising at least one of CO, $CO_2$, or $CO_2$ plus $H_2$ to a bioreactor comprising a culture of at least one acetogenic carboxydotrophic microorganism in a liquid nutrient medium to produce at least one product selected from the group consisting of ethanol, 2,3-butanediol, lactate, succinate, methyl ethyl ketone, 2-butanol, isopropanol, propanediol, and acetoin, the process characterized in that the concentration of at least one nutrient selected from the group consisting of vitamin B1, vitamin B5, and vitamin B7; wherein the concentration of vitamins B5 and B7 is maintained at about 100 to about 4000 µg/g biomass and the concentration of B1 is maintained from about 20 to about 500 µg/g biomass from about.

2. The method of claim 1 where the products are ethanol and 2,3-butanediol.

3. The method of claim 2, wherein the production of 2,3-butanediol is at least 10 g/L per day.

4. The method of claim 2, wherein the production of 2,3-butanediol is at least 20 g/L per day.

5. The method of claim 2 where the ratio of ethanol: 2,3-butanediol varies from about 4:1 to about 1:1.

6. The method of claim 1, wherein the at least one acetogenic carboxydotrophic microorganism is selected from the group consisting of Clostridium, and Acetobacterium.

7. The method of claim 1, wherein the at least one acetogenic carboxydotrophic microorganism is selected from the group consisting of Clostridium autoethanogenum, *Clostridium ljungdahli, Clostridium carboxidivorans, Clostridium drakei, Clostridium coskatii, Clostridium ragsdalei*, and *Acetobacterium woodii*.

8. The method of claim 1 where the concentration of vitamin B5 in the liquid nutrient medium varies from about 200 to about 4000 µg/g biomass.

9. The method of claim 1 where the concentration of vitamin B5 in the liquid nutrient medium varies from about 200 to about 3000 μg/g biomass.

10. A method for the production of ethanol and 2,3-butanediol by a microbial fermentation, the method comprising:
   providing a gaseous substrate comprising at least one of $CO$, $CO_2$, or $CO_2$ plus H2 to a bioreactor comprising a culture of *Clostridium autoethanogenum* in a liquid nutrient medium to produce at least 2,3-butanediol and ethanol; the process characterized in that the concentration of vitamin B5, is maintained at a concentration from about 2 to about 80 times above a concentration of about 198 μg B5/g-biomass.

11. The method of claim 10 where the ratio of ethanol: 2,3-butanediol varies from about 4:1 to 1:1.

12. A method for the production of ethanol and 2,3-butanediol by a microbial fermentation, the method comprising:
   providing a gaseous substrate comprising at least one of $CO$, $CO_2$, or $CO_2$ plus H2 to a bioreactor comprising a culture of *Clostridium autoethanogenum* in a liquid nutrient medium to produce at least 2,3-butanediol and ethanol; the process characterized in that the concentration of vitamin B5, is maintained at a concentration from about 200 to about 4000 μg/g biomass.

13. The method of claim 12 where the ratio of ethanol: 2,3-butanediol varies from about 4:1 to about 1:1.

14. The method of claim 12 where the concentration of vitamin B5 in the liquid nutrient medium varies from about 200 to about 3000 μg/g biomass.

\* \* \* \* \*